(12) United States Patent
Garnica Garza

(10) Patent No.: US 8,681,937 B2
(45) Date of Patent: Mar. 25, 2014

(54) APPARATUS AND METHOD TO CARRY OUT IMAGE GUIDED RADIOTHERAPY WITH KILO-VOLTAGE X-RAY BEAMS IN THE PRESENCE OF A CONTRAST AGENT

(75) Inventor: Hector Mauricio Garnica Garza, Nuevo Leon (MX)

(73) Assignee: Centro de Investigacion y de Estudios Avanzados del Instituto Politecnico Nacional, Apodaca, Nuevo Leon (MX)

( * ) Notice: Subject to any disclaimer, the term of this patent is extended or adjusted under 35 U.S.C. 154(b) by 410 days.

(21) Appl. No.: 13/192,882

(22) Filed: Jul. 28, 2011

(65) Prior Publication Data
US 2012/0027162 A1 Feb. 2, 2012

(30) Foreign Application Priority Data
Jul. 29, 2010 (MX) .................... MX/a/2010/008470

(51) Int. Cl.
*A61N 5/10* (2006.01)
(52) U.S. Cl.
USPC .......................................................... 378/65
(58) Field of Classification Search
USPC ......................................................... 378/65
See application file for complete search history.

(56) References Cited

U.S. PATENT DOCUMENTS 5,207,233 A 5/1993 Barnes
7,603,164 B2 10/2009 Uematsu

FOREIGN PATENT DOCUMENTS

WO 2005036061 A2 4/2005
WO 2007133932 A2 11/2007

*Primary Examiner* — Courtney Thomas
(74) *Attorney, Agent, or Firm* — Fraser Clemens Martin & Miller LLC; J. Douglas Miller

(57) ABSTRACT

The present invention is related to an apparatus and method to carry out image-guided radiotherapy or radiosurgical treatments using Kilovoltage X-ray beams; one of the problems with the clinical application of this treatment consists in the absorbed dosage imparted unto a point within the subject to be irradiated depends on the local concentration of the contrast agent at that point, and the lack of properly quantifying the presence of the contrast agent at each point of the tumor or malformation to be irradiated results in a significant decrease in the quality of the treatment; the method and apparatus of the present invention resolve this and other problems. The Method consists of the following steps: a) determining the geometry of the patient and the concentration of the contrast agent at each point of the same, b) planning of treatment, and c) irradiating of the tumor or malformation; the apparatus includes a system to obtain three-dimensional images of the patient, a plurality of X-ray generating sources, a system to automatically position said X-ray generating sources in such a way that the radiation produced is directed towards the site to be irradiated in the patient, and a computer controlled system.

15 Claims, 11 Drawing Sheets

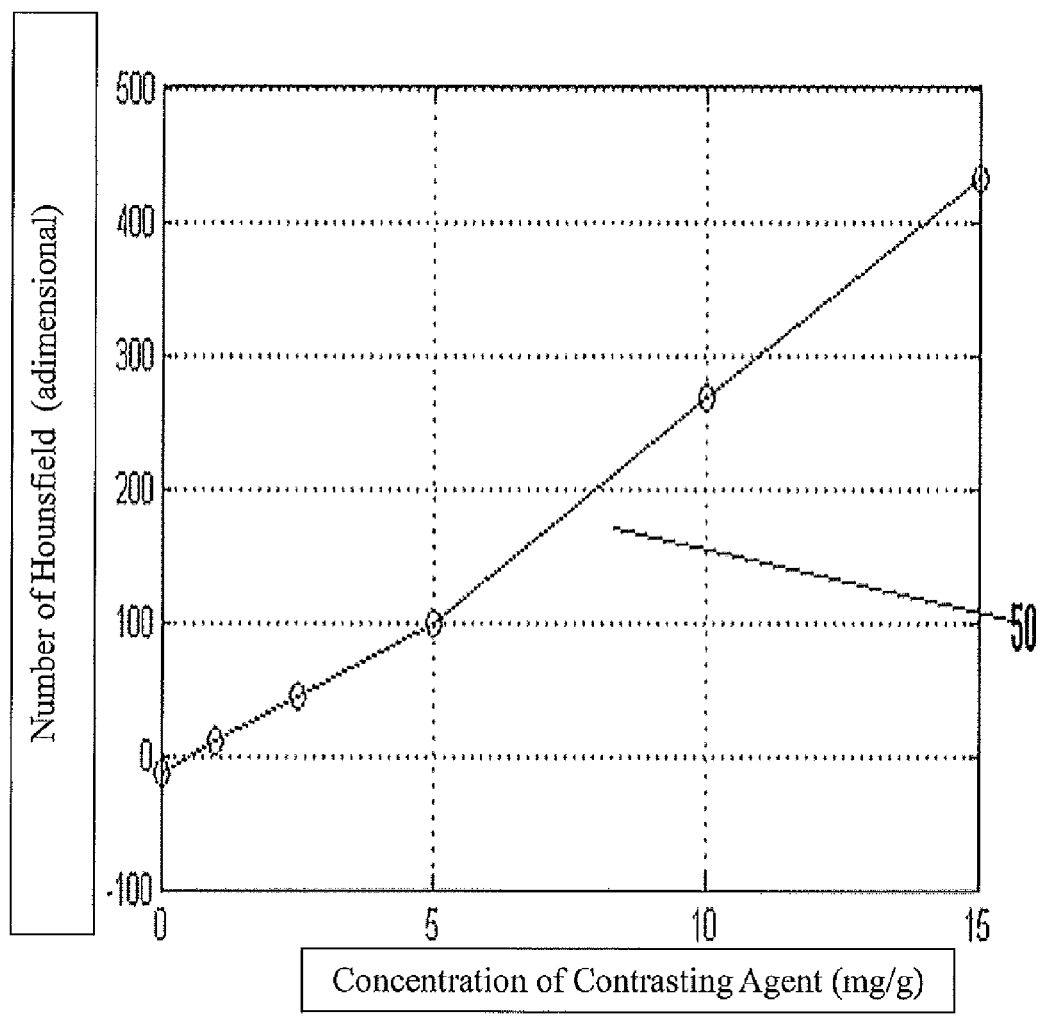
Fig. 4.1

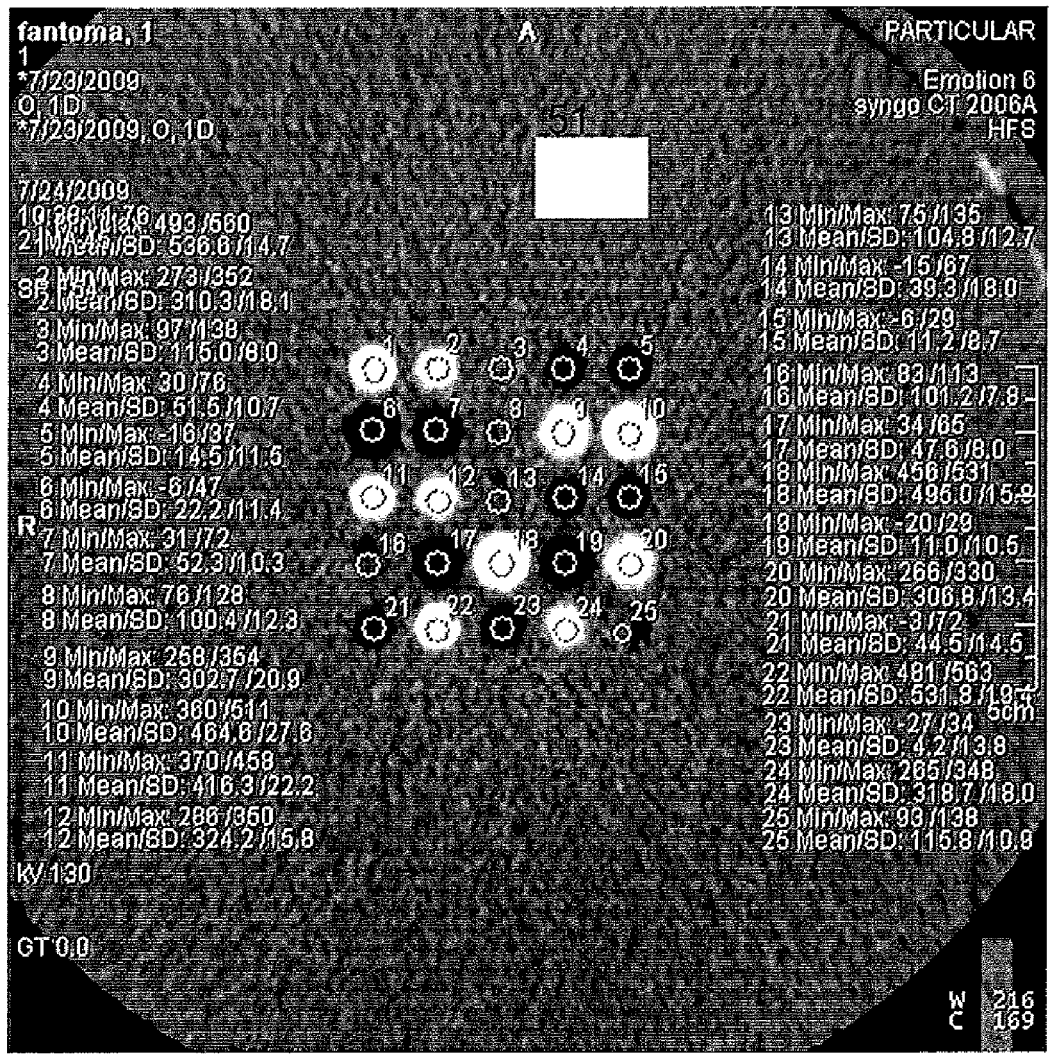
Fig. 4.2

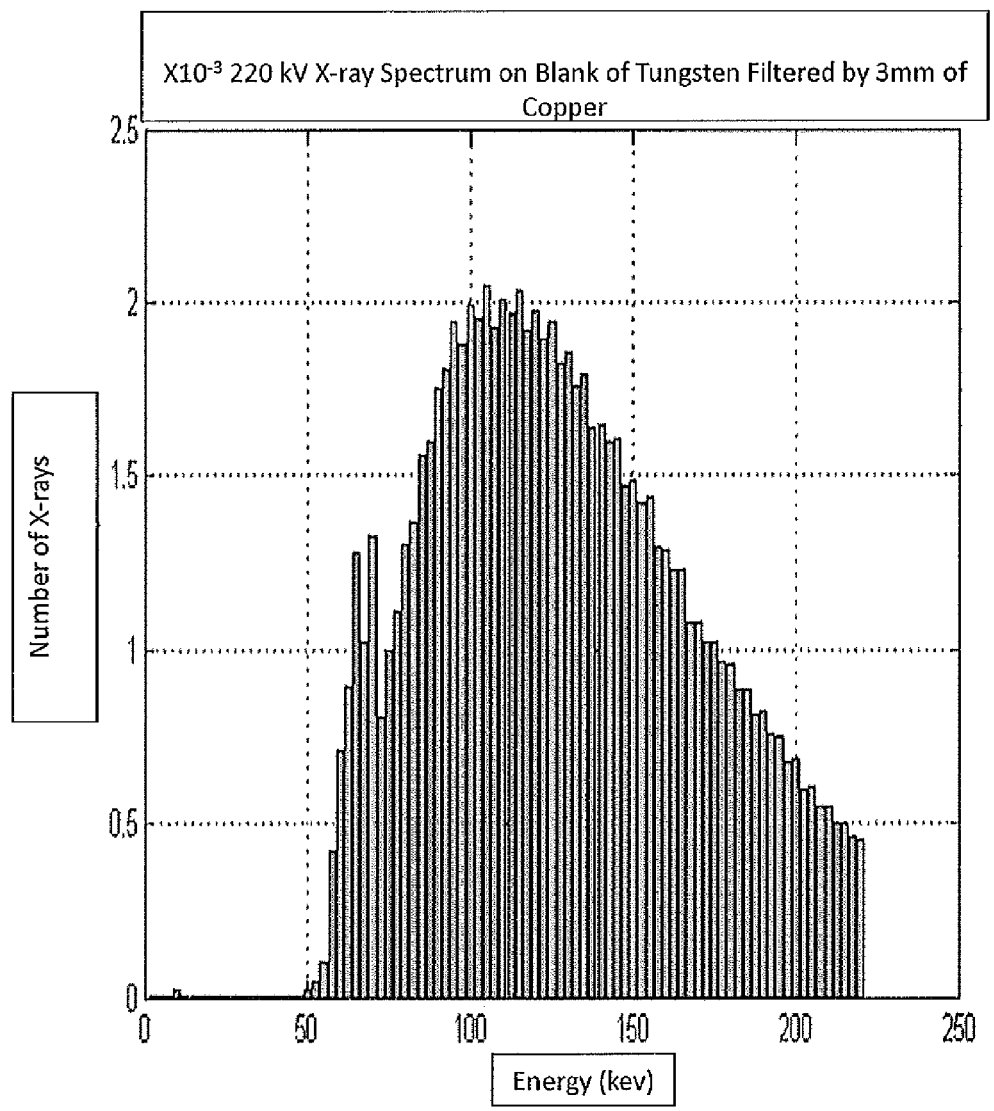
Fig 5.1

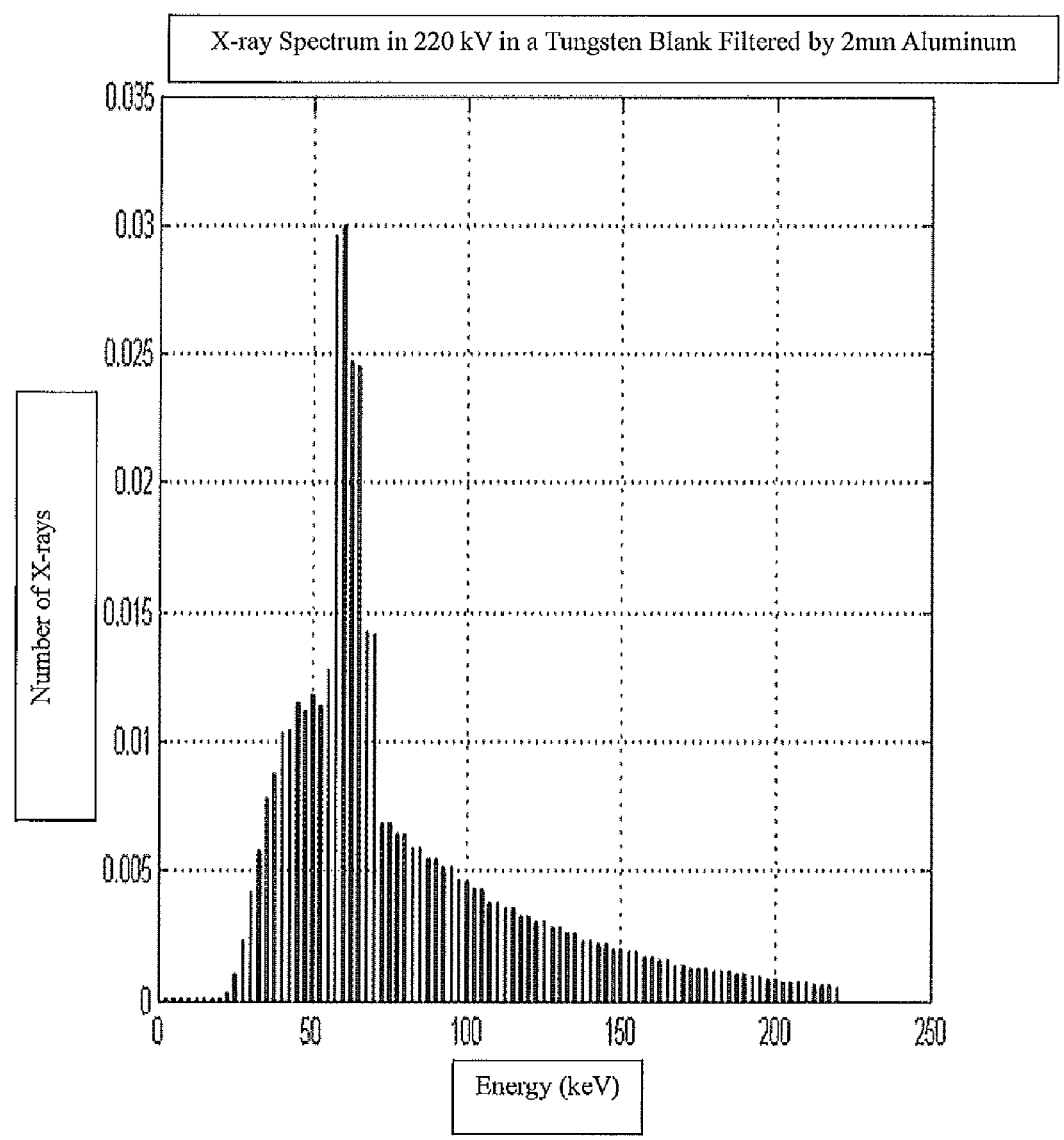
Fig. 5.2

APPARATUS AND METHOD TO CARRY OUT IMAGE GUIDED RADIOTHERAPY WITH KILO-VOLTAGE X-RAY BEAMS IN THE PRESENCE OF A CONTRAST AGENT

CROSS-REFERENCE TO RELATED APPLICATION

This application claims the benefit of Mexican Patent Application Serial No. MX/a/2010/008470 filed on Jul. 29, 2010.

FIELD OF THE INVENTION

The present invention lies in the field of radiotherapy and radio surgery.

BACKGROUND OF THE INVENTION

The present invention is related to an apparatus and a method to carry out radiotherapeutic or radiosurgical treatments using kilovoltage X-ray beams, that is, those whose energy spectrum lies within the range varying between 20 keV to 500 keV. The term image guided radiotherapy is used in reference to the combination of an image acquisition system and a radiation generating ionizing equipment (X-rays, electrons, protons, neutrons and others) used to deliver radiation doses to any structure which can be, but is not limited to, a tumor or an arterio-venous malformation (AVM). The system for image acquisition, through the obtaining of a series of radiologic images, is in charge of "guiding" the way in which the ionizing radiation beam is directed towards the object to be treated in such a way that the beams are aimed towards the tumor or AVM, attempting to minimize the radiation to the healthy tissues and structures which surround it. The image acquisition system can consist of a computerized axial tomography (CAT), a nuclear magnetic resonance imaging (NMRI), cone beam computerized tomography system (CBCT), or stereo graphic projections obtained through a conventional digital radiographic system.

The technology available for the treatment of tumors or AVMs using ionizing radiations has evolved beginning from the kilovoltage X-ray machines, the cesium or cobalt sources (with energies of 0.66 MeV and 1.25 MeV respectively), up to the modern computer-controlled linear accelerators capable of producing radiation beams with peak energies of up to 25 MeV for X-rays and of up to 20 MeV for electrons. The purpose of trying to reach high energies for the treatment of non-surface tumors in radiotherapy is tied to the physics of the interactions between the radiation and matter: the beam with the highest energy has not only greater penetration power (greater absorbed dose at depth as compared to lower energy beams), but also the absorbed dose at points close to the surface of the objects being irradiated is lesser in correlation to the increase of the beam's energy. For example, when an X-ray beam with maximum spectral energy of 15 MeV is compared to an X-ray beam with maximum spectral energy of 150 keV, the radiation doses at a depth of 10 cm, typical for example in prostate tumors, is 80% of the maximum for the 15 MeV beam and only 35% of the maximum for the 150 keV beam. It is worth mentioning, however, that as the energy of the radiation beam being used increases, so does the economic cost not only of the apparatus which generates radiation, but also of the installations necessary to accommodate it, given the amount of shielding required to confine the radiation emitted to the treatment room. The kilovoltage x-ray beams, on the other hand, can be produced at a fraction of the cost of the megavoltage x-ray beams, the installations necessary to accommodate them require much less shielding and the generating equipment is compact and requires simple maintenance. However, given the low penetration of this type of radiation, its use has been limited to the treatment of surface tumors, that is, those found at no greater depth than 2 cm in the patient. For tumors found at a greater depth, using kilovoltage X-rays exposes the healthy tissues which are found in the beam's trajectory before reaching the tumor, to excess radiation.

The problem is the following: given the low penetration of the X-ray beams with energies in the 20 KeV-500 KeV range, very little radiation reaches the tumor, and that which does reach it, is inefficiently absorbed given the uncertain nature of the interaction of the radiation with the matter. At the beginning of the 1980's, Mello and collaborators reported that the use of iodinated agents (solutions with an iodine base) incorporated into experimental tumors, those implanted into animals for laboratory study, would show better response when they were radiated with kilovoltage X-rays as compared to tumors lacking the incorporation of the iodinated agents (Mello R S et. al. *Phys. Med. Biol*. Vol 10 pp 75-78, 1983). The iodine or gadolinium based compounds absorb the X-rays in a preferred manner in this energy range, given mainly to the photoelectric effect and thus are routinely used in diagnostic radiology to highlight organ visibility. This application in particular gives rise to the term "contrast agent".

It is important to highlight that this effect only occurs for the combination of the contrast agent and kilovoltage X-rays with energies ranging between 40 keV to 150 keV, given that at these energies, the main interaction mechanism between the X-rays and the matter is through the photoelectric effect, which is not the case for the beams with energies in the megavoltage range, as they interact mainly through other mechanisms (Compton effect and pair production). This increase in the X-ray absorption caused by the incorporation of the contrast agent into the tumor is responsible for the better response of the tumor to the radiation observed by Mello and collaborators. In 1994, the first attempt to clinically apply this treatment embodiment was reported: Rose and collaborators used a Computerized Tomography Scanner, with an X-ray spectrum with energy spikes in an order of 150 keV, to carry out treatments of cerebral tumors using an iodine based contrast agent (Rose J H et. Al. Int. J. Radiat. Oncol. Biol. Phys. Vol. 30 pp. 24-25, 1994). The treatment was administered in conjunction with conventional radiotherapy using megavoltage beams, and cerebral tumors were chosen given that the depths at which such tumors are found generally do not exceed 5 cm. Only a small fraction of the total dose was administered with the axial tomography scanner. The concentration of the contrast agent reported in the tumor was that of 10 mg of iodine per gram of tissue (10 mg-l/g), however, this is merely an estimate by the scientists who carried out the study and not a quantitative measurement.

Recently, it has been reported that experimental contrast agents based on gold nanoparticles dissolved in a saline solution produce a similar effect to that reported by Mello and collaborators, with the advantage that in principle, metallic nanoparticles with a diameter in the 2 nm range, accumulate preferentially in the tumor (Hainfeld J F et. al. Phys. Med. Biol. Vol. 49 pp N309-N315), 2004). Recently it has been shown that using rotational irradiation techniques, it is possible to irradiate tumors at depths of 10-12 cm using the clinically available iodine or gadolinium based contrast agents (Garnica-Garza H M Technol. Cancer Res. Treat. Vol. 9 pp 271-278, 2010) as well as experimental contrast agents such as could be those based on metallic nanoparticles, particularly gold and bismuth (Garnica-Garza H M Phys. Med. Biol. Vol. 54 pp 5411-5425, 2009).

It has also been shown that even though the treatments can be acceptable with regards to the radiation doses received by the tumor, certain bone structures receive doses which are too high. Additionally, given that the bone structures which surround the tumor attenuate in a very pronounced way the X-rays which are directed unto the tumor, the resulting doses which are absorbed by the tumor are very non-uniform. It has also been shown that the radiation beams must be filtered in a significant manner to remove the very low energy X-rays, as these low energy X-rays interact at a very short distance from the surface, increasing the dosage absorbed by the skin which represents a serious limitation to the clinical application of this treatment embodiment. The need to filter the used X-ray beams presents a problem to the possible clinical application of this treatment technique, seeing that upon filtering an X-ray beam in a significant manner, the amount of radiation which reaches the tumor is also reduced, resulting in longer treatment times, which represents a serious disadvantage. Another of the problems with the clinical application of this new treatment embodiment arises from the fact that the absorbed doses imparted to a point within the subject to be irradiated depends on the local concentration of the contrast agent at that specific point, and not quantifying such a concentration in an appropriate manner at each point within the tumor or malformation to be irradiated results in the significant degradation in the quality of the treatment (Garnica-Garza H M Phys. Med. Biol. Vol. 54 pp 5411-5425, 2009).

In the state of the art there exist several applications and patents which refer to equipment and methods for delivering radiotherapy, some of which are described as follows:

Application number; 9807896. Title: Therapy and Surgical Treatment System by means of Radiation and Methods of use of the same. The summary which is published for this invention provides the following: A radio surgical and radiotherapy system to provide a diagnostic and locating image of the object through tridimensional mapping of the patient in third dimension by such means as the CT Scanner or MRI, placement of the patient on an examining table with a four degree freedom of movement, and a stereotactic therapy unit with cobalt 60 is provided which incorporates multiple sources to irradiate an object; methods of radiosurgery and radiotherapy which use the system are also provided; a configuration of the combination of the radiation source, 360° rotation characteristics of the therapy unit and the movement of the table will allow irradiating any size and shape of the object at therapeutic levels while the radiation exposure to surrounding healthy tissue is minimized; also a stopper of radiation beams is provided, which captures more than 80 percent and preferably more than 90% of the radiation of the sources of radiation.

Application number: PA/a/2006/003787. Title: Planning System, Method and Apparatus for Radiation Therapy. The published summary of this invention provides the following: A system and the associated methods to determine optimal radiation beam arrangement are described. The system includes a computer based planning apparatus which optimizes the treatment plan, which has a memory and an entrance device which is in communication with the computer to optimize the treatment plan to provide access to the operator to control the software functions in order to optimize the plan. A device which obtains images is in communication with the optimizing computer for the treatment plan, through a communications network, in order to provide a part of the image of the objective tumor's volume and the volume of the structure which is not the objective. The software for the optimizing plan is obtained computationally and later optimizes a proposed radiation beam arrangement, repeating based on the constrictions, to form an optimized arrangement of the radiation beam. An administering therapeutic device with radiation, according, in communication with the computer optimizing the treatment plan, through the communication network, later applies the optimized radiation beam arrangement to the patient.

Application number: WO 2007/133932. Title: Deforming Register for Radiotherapy Images directed by Images. The published summary of this invention provides the following: A system and method to develop radiotherapy plans and a system and method to develop a radiotherapy plan to be used in radiotherapy treatments are disclosed. A radiotherapy plan is developed using a register of medical images. The register is based on the identification of the signals found within the internal structures of the body.

U.S. Pat. No. 7,603,164 B2. Title: Compound System for Radiotherapy. The published summary of this invention provides the following: A compound system for radiotherapy includes a CT scanner to prove the position of the affected portion to be irradiated in a patient, an apparatus for irradiating is available, based on the positional information of the affected portion verified by the CT scanner, of the patient in a specific position in which the affected portion is aligned in an irradiating position, and the carrying out of the irradiation to the affected portion, a common bed used for the CT scanner and the irradiation apparatus, in a state where the patient is in prone position on the common bed and means of movement to move the patient from the CT scanner to a specific position within the irradiation apparatus. The means of movement move the patient on the common bed to a specific position by causing either linear movement of the CT scanner and the irradiation apparatus, linear movement of the CT scanner and curving movement of the irradiation apparatus, curving movement of the scanner and the irradiation apparatus and linear movement of the CT scanner, linear movement of the CT scanner and the common bed, and linear movement of the CT scanner and curving movement of the common bed. With this compound system, at the time of radiotherapy to the tumor or similar, the affected portion can be irradiated in a state in which the position of the affected portion aligned by a CT scanner is maintained with precision. As a result, it is possible to significantly increase the control with exactitude of the position of the affected portion in radiotherapy and as such significantly increase the effect of radiotherapy.

U.S. Pat. No. 5,207,223. Title: Apparatus and Method for the Development of Stereotactic Surgery. The published summary of this invention provides the following: A method and apparatus are available to selectively irradiate a blank within a patient. A three dimensional sketch of a region surrounding the target is provided. A radiation emitting apparatus emits a collimated beam. Diagnostic beams at a known angle other than zero from each other travel through the sketched region. These diagnostic beams produce projection images within the sketched region. Electronic representations of the images are compared to the reference data, in such a way that the target is located. The relative positions of the emitting apparatus and the live organism are adjusted in such a way that the collimated beam is focused unto the target region. The comparison is repeated at small time intervals and when the comparison thus indicates, the adjustment step is repeated as needed, and in such a way that the collimated beam remains focused on the blank region.

The patents and applications, whose summaries are described above, do not precede the invention of the present application and therefore shall be described as follows.

In U.S. Pat. No. 7,603,164 B2, a linear accelerator (apparatus which produces X-rays with peak energies from 4 MeV up to 20 MeV) is coupled to a computerized tomography scanner (CAT), to snap images of the patient's internal geometry in order to determine where to aim the linear accelerator to. So this is indeed radiotherapy system which is guided by images. A significant problem with this patent is that the use of the CAT scanner and the accelerator cannot be simultaneous given the large volume of both apparatuses, it is impossible to take the image during the irradiation of the patient, so first the image is taken, the scanner is moved away from the patient, and the accelerator is placed then proceeding to irradiate the tumor. In the present invention to be described, given that the X-ray equipment with energy in the kilovoltage range (necessary to be used in conjunction with a contrast agent) is compact (weight ~50 kg compared to the 2 to 3 tons of a linear accelerator) and given the design which is used, the taking of radiological images can be done in real time during the irradiation of the tumor, which is a great advantage, as it has been proven that tumors move during the irradiation of the same (due to, for example, the patient's breathing movements, the beatings of the heart etc.) in such a way that the tumor's movement can be followed in real time and the necessary corrections be made, also in real time to aim the X-ray beams unto the tumor's actual position and not where it was 3 or 4 minutes prior. The use of a plurality of X-ray sources to irradiate the tumor is also a significant difference, given that in U.S. Pat. No. 7,603,164 only one linear accelerator is used (that is, one source) to irradiate the tumor.

In U.S. Pat. No. 5,207,223, one linear accelerator and two diagnostic X-ray tubes are used, placed at a certain angle from each other to determine the position of the tumor or malformation during treatment and to thus carry out image guided radiotherapy procedures. A problem with this apparatus is that the diagnostic X-ray equipment used only provides bi-dimensional images of the site to be irradiated, so that even though it is possible to determine lateral tumor movements with respect to the image plane of the tumor, it is impossible to determine movements in the direction of the X-ray beam's incidence. So the tumor movement can only be tracked in two dimensions. Another limiting factor of this apparatus is that it only uses one collimated radiation source to produce circular beams with variable diameter, not taking into account the possibility of producing fields in other geometric forms. In the present invention a plurality of treatment sources are used capable of producing fields with varied geometric forms in addition to being capable of monitoring the tumor or malformation's position in three dimensions in real time.

In patent application WO 2007/133932, a method is described to effect radiotherapy planning using radiologic images taken before and during radiation treatment. The method uses internal markers, which can be bone structures in the patient or tiny gold spheres surgically inserted into the tumor, to determine how organs and tissues are deformed in a patient during the radiation application due to the physiologic movements of said patient. The method described in said application employs a series of computerized tomography images, taken at different time instances, and uses them to carry out a radiotherapy plan. A problem with this method is that it assumes the same pattern of deformity of the patient's inner structures occurs both at the time at which the images were taken as at the time of the patient's radiation treatment, which is not necessarily the case, given that physiologic movements are variable. Additionally, no technique is described to monitor the movement and deformation of the inner structures in real time during treatment.

In patent application number 9807896, a radiotherapy and radiosurgical apparatus is described which uses a plurality of sources in conjunction with a computerized tomography scanner or nuclear magnetic resonance scanner to identify the site to be irradiated. The computerized tomography scanner (CAT) or nuclear magnetic resonance (NMR) is found placed in separate and opposite sites to the radiation sources. The system includes a support table for the patient which can rotate up to 180° which is placed between the tomography scanner or nuclear resonance and the apparatus which contains the radiation sources, in such a way that through the rotation of the patient's support table it is possible to place said patient in the scanner to identify the geometry of the site to be irradiated and afterwards, by means of an opposite rotation of the support table, place it in the position in which it will be irradiated. A problem with this is that it is not possible to use the CAT scanner or NMR in a simultaneous manner with the application of radiation on the tumor or malformation, that is, first the images of the geometry of the site to be treated with the CAT scanner or NMR are obtained, and afterwards the radiation can be applied. As was previously mentioned, this is not the most convenient given that the tumor or malformation can move during the application of radiation. Another problem with the described invention is that the plurality of radiation sources point unto a same focal point, and additionally, are contained in a single mechanism, that is, they lack independent movement from one another so that they all must be pointed to the same point and with the same orientation. As shall be described in detail later, the apparatus and method described in the present invention differ considerably from the patent application just described, seeing that, firstly, with the apparatus object of the present invention it is possible to accomplish the monitoring in real time of the position of the tumor or malformation during the application of radiation. Additionally, the plurality of sources which form part of the present invention are capable of irradiating the tumor or malformation from a plurality of positions not necessarily contained on a plane in addition to also irradiating more than one region of the tumor or malformation simultaneously, which is not the case in the patent application previously described and which grants flexibility at the time of irradiating the tumor or malformation, which is lacking in the apparatus of the described patent application.

Patent application number PA/a/2006/003787 presents an associated computing method and system to effect the planning of radiotherapy treatments using optimization algorithms. A planning of radiotherapy treatments basically consists of simulating in the computer the effects which different pertinent parameters on the radiation field used (radiation beam energy, collimation type, angle of incidence of the radiation beam on the patient, among others) have on the absorbed dose distributions which result in the volume of the patient to be treated. A problem with the invention presented in said patent application is that the system is designed to produce plans for high energy radiation treatments emanating from a linear accelerator or cobalt unit 60, which interacts with matter in a different way than the beams of low energy radiation, particularly in the way in which they are absorbed by high density structures, as can be, for example, bone structures. In this sense, the optimization of a radio therapeutic plan intended for a high energy radiation beam is not usable for a low energy beam.

From the above, it is gathered that to clinically implement a treatment technique for tumors and malformations using kilovoltage beams in conjunction with contrast agents, it is necessary to have a method and apparatus which together provide a complete radiotherapy and/or radiosurgical system capable of overcoming all and each of the limitations and problems previously described. In summary, to overcome all of these problems, one clinical implementation of this treatment embodiment requires a radiotherapy and/or radio surgical system with the following characteristics:

1. The system must allow the obtaining of three-dimensional anatomical images during the application of radiation to the patient, with the end purpose of monitoring not only the position of the tumor or malformation but also that of the bone structures which could surround it. Radiotherapy systems already exist which gather images of the patient with the end purpose of monitoring the position of the tumor, however, they only do so immediately before or after the application of the radiation and not during the application of said radiation.
2. The system must allow for spatial quantification of the presence of the contrast agent in the subject to be irradiated. By spatial quantification it must be understood that the system provides the three-dimensional distribution of the contrast agent within the patient. This quantification of the contrast agent must be carried out in real time during the application of radiation to the patient.
3. Based on the distribution of the contrast agent within the subject to be irradiated, the system must be capable of determining the combination of radiation beams whose application to the irradiated subject will result in a distribution of absorbed doses which accomplishes the treatment criteria specified by the radiation-oncologist physician.
4. The system must be capable of producing X-ray beams with a plurality of energy spectra in such a way that it provides a wide flexibility for the selection of the appropriate beam energy.
5. The system must be capable of producing reasonable treatment times, that is, in the 2 or 3 minute range.
6. To maximally reduce the dosages to the surface and be capable of reducing the attenuation of the radiation beam due to the bone structures, the system must have the necessary flexibility to allow the radiation beams to be aimed at the tumor from a plurality of sites not necessarily contained on a single plane surrounding the subject to be irradiated.

Thus it is an objective of the present invention, to provide a system for the obtaining of three-dimensional anatomic images during the application of radiation to a patient with the end purpose of monitoring not only the position of the tumor or malformation, but also that of the bone structures which could surround said tumor.

Another objective of the present invention is to provide a system to spatially quantify the presence of a contrast agent in the subject to be irradiated, providing a three-dimensional distribution of the contrast agent within the patient.

Yet another objective of the present invention is that of providing a system which, based on the distribution of the contrast agent within the subject to be irradiated, determines the combination of radiation beams whose application to the irradiated subject results in a distribution of absorbed dose which satisfies the treatment criteria set by the radio-oncologist physician.

Another objective of the present invention is that of supplying a system which produces X-ray beams with a plurality of energy spectra in such a way that it provides a greater flexibility at the time of selecting the radiation beams.

Yet an additional objective of the present invention is that of providing a system which produces reasonable treatment times, that is, in the 2 to 3 minute range.

A further objective of the present invention is that of providing a system which reduces to the furthest extent possible the maximum absorbed dose imparted to the surface of the patient and is capable of reducing the attenuation of the radiation beam produced by the bone structures.

Lastly, another objective of the present invention is that of providing a system which possesses the necessary flexibility to allow the radiation beams be pointed to the tumor from a plurality of sites not necessarily contained on a single plane surrounding the subject to be irradiated.

Following are details of the method and apparatus of the present invention to carry out radiotherapy and/or radiosurgery with kilovoltage X-ray beams, in the presence of contrast agents incorporated into the subject to be irradiated, which in combination allow for the resolution of all and each of the problems associated with this treatment previously described.

BRIEF DESCRIPTION OF THE DRAWINGS

FIG. 4.1 shows a calibration curve to obtain the concentration of the contrast agent as a function of the signal provided by the 3-D image acquisition system.

FIG. 4.2 refers to an image of each of the cells into which the contrast agent solution is deposited.

FIG. 5.1 shows an X-ray spectrum and the effect which a copper filter has on said spectrum.

FIG. 5.2 refers to an X-ray spectrum and the effect which an aluminum filter has on said spectrum.

DETAILED DESCRIPTION OF THE INVENTION

Figure 1A:
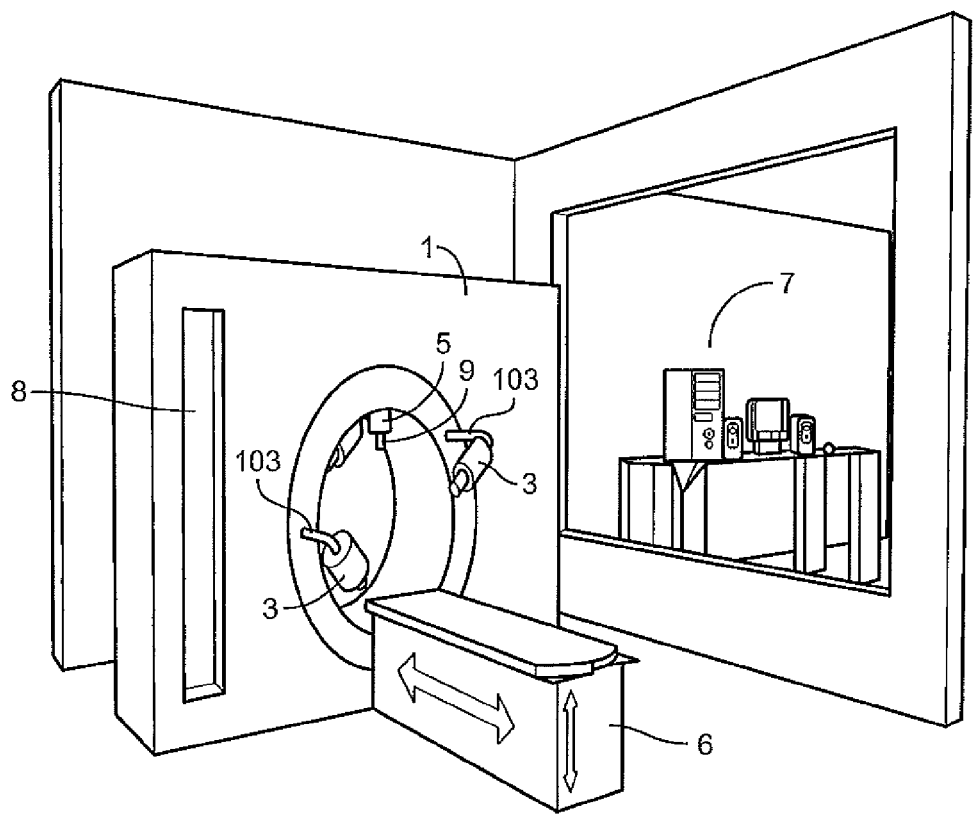
In FIG. 1A shows an illustration of the apparatus of the present invention, including the system for 3-D image acquisition and three X-ray generator systems mounted on mechanical arms. It is important to highlight that three X-ray systems are shown for the sake of the figure's clarity and not as limiting the invention, given that it is possible to use a different number of X-ray generators.

The present invention provides an apparatus for radiotherapy and/or radiosurgery which includes a system for the obtention of three-dimensional images of the patient (1), a plurality of X-ray generating sources (3), a system to automatically position said X-ray generating sources in such a way that the radiation produced be directed to the site to be irradiated in the patient, and a computer to automatically control the system (8). For the sake of clarity, the present invention is described through an example, without this implying or signaling limitations on the apparatus and revealed techniques.

The central objective of radiotherapy and/or radiosurgery is to maximize radiation absorbed dose imparted to the tumor while at the same time minimizing the radiation absorbed dose received by the surrounding healthy tissues and structures. To accomplish such in conventional radiotherapy, the following conditions are required:

a) Determine by means of radiological images the patient's geometry, that is, the position of the tumor or malformation relative to the surface and also relative to other structures and tissues of interest.

b) Treatment planning. Based on the patient's geometry, the energy, number and angles of incidence on the tumor are determined for each beam in order to obtain the best absorbed dose distribution as determined by the radiooncologist physician. This process is generally undertaken with the help of specialized computer software.

c) Additionally, in image guided radiotherapy, radiological images taken during the application of radiation to the patient are employed to monitor the position of the tumor or malformation, which can move due to the physiologic movement of the patient, such as heartbeats and breathing movements.

As was previously mentioned, the amount of x-ray radiation absorbed at a given point in a medium which contains a certain concentration of a contrast agent depends on the magnitude of said concentration at such point. Thus, it should be anticipated that in radiotherapy with kilovoltage X-rays in the presence of contrast agents, it shall be necessary to have a method which allows determining the amount of contrast agent present at each point of the irradiated volume. Based on this, the detailed description of the invention shall cover the three treatment aspects of the application of ionizing radiation to a tumor or malformation, namely:

I. Determining the patient's geometry and the concentration of contrast agent at each point in the same.
II. The planning of the treatment.
III. Irradiation of the tumor or malformation.

It is important to point out that given the nature of method and apparatus of the present invention, these three processes do not necessarily need to be carried out in the above mentioned order, seeing as in the revealed method it is possible to make corrections to the treatment in real time during the unfolding of said treatment. It should be understood then that the fact that the present invention is described in a particular order does not imply a limitation to said invention.

Determination of the Contrast Agent Concentration in the Patient

Figure 8:
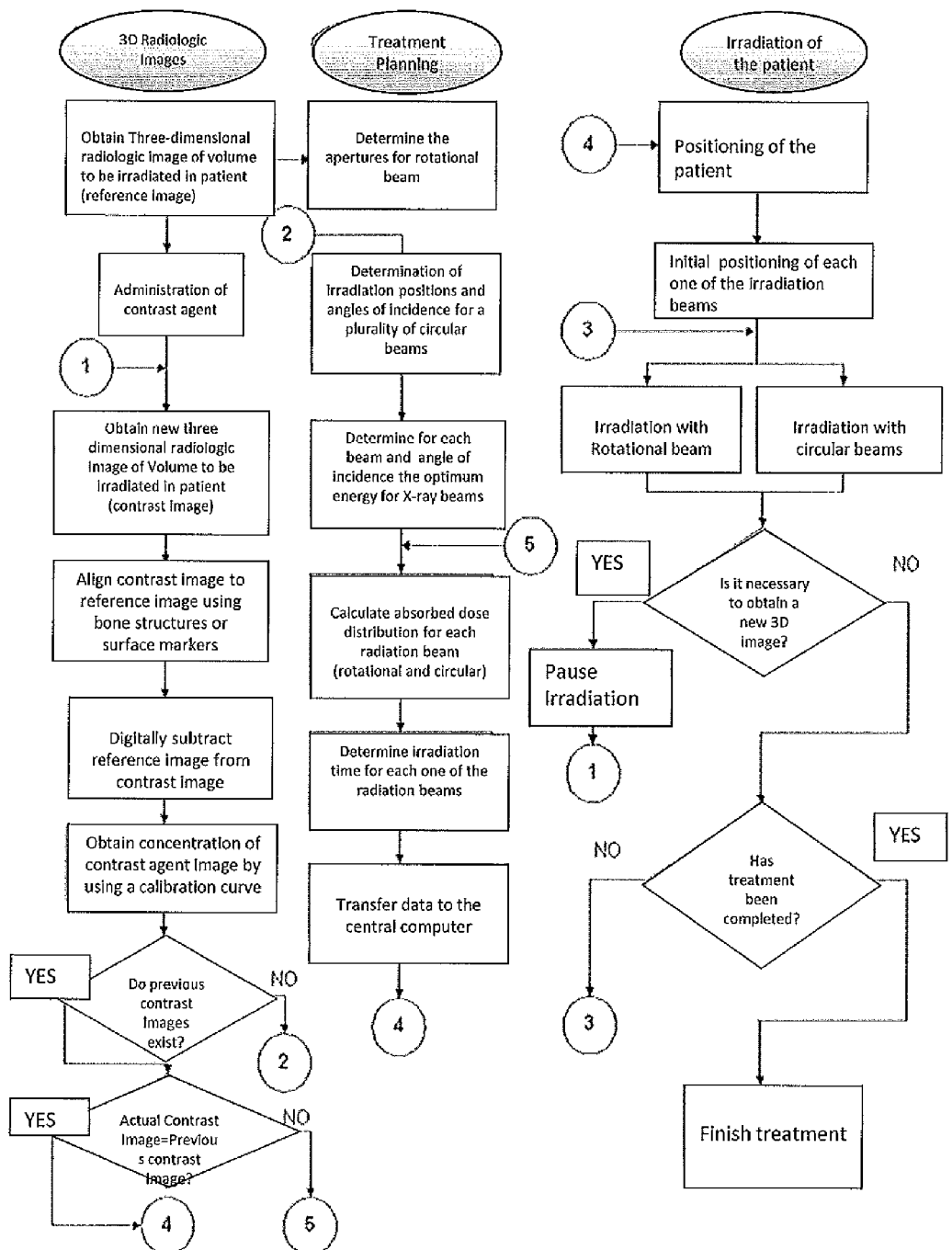
FIG. 8 shows a flow diagram which illustrates the technique to carry out the radiotherapy and/or radiosurgery treatment with the apparatus object of the present invention.

As was shown in FIG. 1A, the system for the acquisition of 3D images (1) is used to obtain a three dimensional image of a portion of the patient to be treated; this step is shown in the first block of the first column in FIG. 8. The image taken provides information about the geometry of the volume to be irradiated, geometry being understood as the location of the tumor with respect to the surface of the patient as well as the distance of said tumor from the tissues and structures which surround it.

This image is used by the treatment planning computer (7) to establish the position of each one of the structures of interest with respect to a reference frame which, for illustration's purposes can be taken with respect to the treatment room, with the understanding that other possibilities exist.

An additional purpose of this image is to serve as a reference to determine the amount of contrast agent present in each one of the organs and tissues of interest once the contrast agent is administered to the patient.

Figure 7:
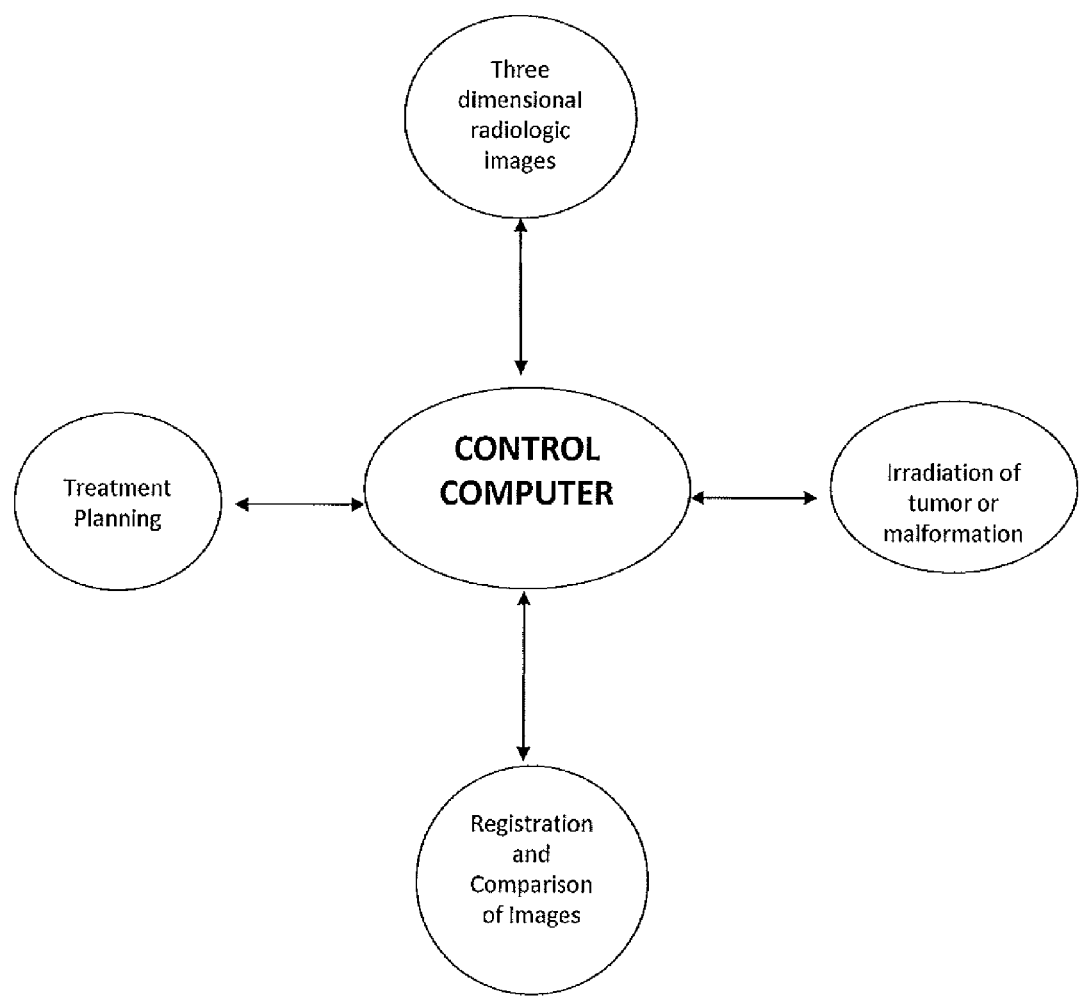
FIG. 7 shows a diagram which illustrates the interaction of the different processes to be carried out during the treatment of the tumor or malformation with the apparatus and method object of the present invention.

According to the diagram in FIG. 7 and following the flow diagram in FIG. 8, the step which follows is the administering of the contrast agent to the patient, this step is shown on the second block of the first column in FIG. 8. As an example, the contrast agent can be, but is not limited to, iodine, gadolinium or agents formed by metallic nanoparticles. As has been previously mentioned, the radiation absorbed dose at a given point in the irradiated volume depends on the concentration of the contrast agent at that particular point, as well as on the concentration at nearby points, and thus, it is necessary to determine this parameter.

Once the contrast agent is found circulating within the patient, which can be determined for example by means of a computerized tomography image obtained in scout mode, the next step is to take a second computerized tomography image with the same scanning parameters (peak potential, x-ray tube current, and slice width) as the reference image previously described; this step corresponds to the third block of the first line in FIG. 8.

To determine the amount of the contrast agent at each point in the patient, a calibration curve (50) is used, shown in FIG. 4.1. This calibration curve, which shall be obtained before the treatment is carried out, is obtained using known concentrations of the contrast agent embedded in an anthropomorphic phantom (a device with similar dimensions and materials to those found in the human body), which are scanned by the computerized tomography scanner to obtain images of each of the compartments into which a solution containing the contrast agent are deposited; an example of said image is shown in FIG. 4.2. By plotting the signal in each image pixel against the known concentration of the contrast agent, the calibration curve (50) is obtained as shown in FIG. 4.1. This step corresponds to the sixth block of the first line in FIG. 8.

Once the two tomography images are obtained, both images are digitally aligned using, as an example, the patient's bone structures or markers placed on the surface of the patient. This corresponds to the fourth block of the first column of the flow diagram in FIG. 8. After which, the reference image is subtracted digitally from the image obtained with the contrast agent, which results in a residual image of the presence of the contrast agent in the patient, this step is shown in block 5 of the first column in FIG. 8. Then, using the calibration curve (50), each pixel of the residual image is assigned a concentration of the contrast agent according to the value of the signal present in said pixel. This procedure provides what we shall call a concentration-of-contrast-agent image. The reference image in conjunction with the concentration of contrast agent image is used to carry out what in radiotherapy and/or radiosurgery is referred to as a "treatment plan".

Treatment Planning

The process of treatment planning basically consists of selecting a series of parameters (the number of radiation beams, the angles of incidence on the tumor for each beam, the energy of each beam, among others), in such a way that the distribution of absorbed dose imparted to the tumor satisfies the criteria established by the physician prescribing the treatment, who typically specifies a minimum absorbed dose imparted to the tumor and a maximum permissible dose to the healthy structures and tissues surrounding the tumor. As opposed to radiotherapy and/or radiosurgery using radiation beams with an energy spectrum in the megavoltage range, given the low penetration power of X-rays with energies in the kilovoltage range, the process of selecting the entrance angles for each one of the beams to be used is critical. To satisfy requirements 4, 5 and 6 previously described, the present invention considers two types of radiation beams simultaneously available during the treatment of the tumor or malformation:

A radiation beam produced by a kilovoltage X-ray source (5), which is a compact piece of equipment weighing approximately 50 kg, with a capability to rotate on a plane around the patient, such as is shown in FIG. 1A. This source has a collimator attached to it which allows it to produce radiation fields which conform to the geometric shape of the tumor as seen from the beam's eye view. This radiation beam has the capability of producing different energy spectra by means of varying, for example, the maximum energy of the electrons incident on the metallic target in order to produce X-rays through the effect known as bremsstrahlung, or by means of using metallic filters of different materials and thickness placed on the exit window of the X-ray tube.

Figure 1:
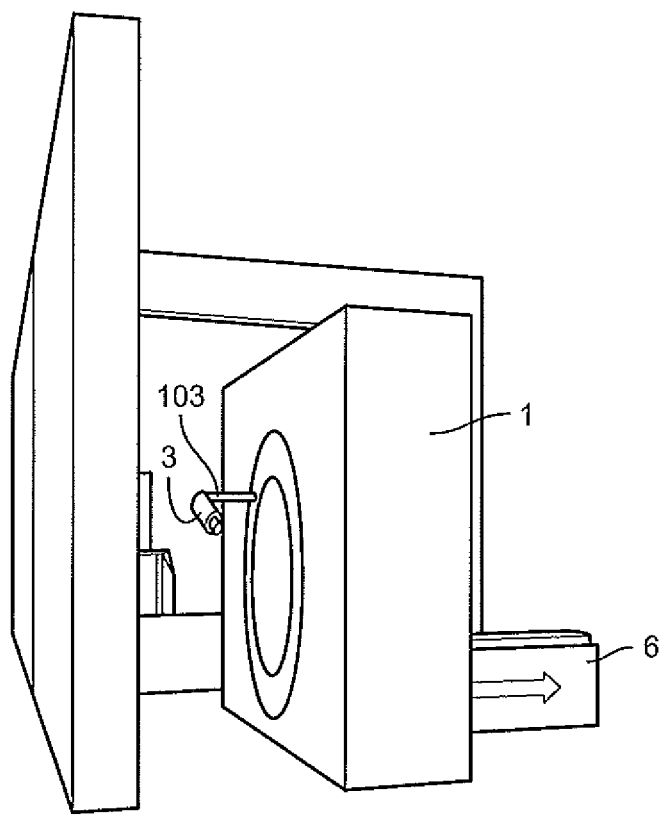
FIG. 1B shows a different perspective of the apparatus of this invention, where another X-ray generator is shown.

A plurality of circular radiation beams generated by a plurality of kilovoltage X-ray sources and whose diameter varies, for example, between 0.5 cm and 2.0 cm. This plurality of radiation beams can be aimed at the tumor or malformation to be treated from a variety of points which are not necessarily confined to a plane, such as is shown in FIGS. 1$a$, 1$b$ and 3. This plurality of radiation beams has the capability of producing different energy spectra by means of varying, for example, the maximum energy of the electrons incident on the metallic target in order to generate X-rays through the effect known as bremsstrahlung, or by means of using metallic filters of different materials and thickness placed on the exit window of the X-ray generator.

These two types of radiation beams can be used simultaneously or separately, depending on what is more convenient for the treatment purposes. The need 4 above, the production of a plurality of energy spectra, is satisfied through the use of this plurality of X-ray sources, as each one of the sources can have a different metallic filter from the ones of the other sources so that a variety of spectra is produced, as is shown in FIGS. 5.1 and 5.2. The use of various radiation sources also satisfies the requirement 5 above, given that the more sources available in a given instance to irradiate a tumor or malformation, the shorter the treatment time will be. Lastly, the need 6 to decrease the absorbed dose to the surface and to avoid the bone structures to the maximum extent possible is satisfied by means of using X-ray beams with varying diameters aimed at the tumor from a plurality of sites not necessarily contained on a same plane. To determine the parameters to be used with each one of the beams to be used in the treatment, namely the energy of each beam, position of the x-ray source and collimation, we use the flow diagram shown in FIG. 8:

i. The first step, corresponding to the first block of the second column in FIG. 8, consists of determining the appropriate collimation for the X-ray source which turns on a plane around the patient. To determine this collimation, the reference image is used, on which, by previous determination on the part of the radiation oncologist, the structures of interest have been delineated or segmented, particularly the tumor or malformation as well as the healthy organs and tissues adjacent to this. As an example and not as a limiting factor, it is possible that the physician decides that the collimation must take place in such a way that the tumor or malformation be irradiated avoiding certain adjacent structures which are necessary to protect.

ii. The determination of the irradiation positions for the plurality of circular beams with varying diameters takes place by means of a computer under the following criteria:
   a. To reduce the radiation dose imparted to the skin, the circular beams are not allowed to cross or intersect at the surface of the subject to be irradiated.
   b. The chosen irradiation position for each source must be such that the radiologic distance from the patient's surface to the site of the tumor or malformation to be irradiated is minimized. The radiologic distance is defined as the product of the geometric distance and the density of the material crossed:

$$s = \Sigma di \times \rho i$$

Where s refers to the radiologic distance, d is the geometric distance and $\rho$ is the density of the material crossed. A summation is used seeing that the medium can contain different types of material: the criteria of minimizing the radiologic distance crossed by the circular beams of variable diameter ensures the avoidance of bone structures given that bone has a much higher density than soft tissue and additionally avoids the areas where there could be contrast agent outside of the tumor or malformation, since the density of the contrast agent is also greater than that of the soft tissue, thus satisfying the previously mentioned requirement 6.

Figure 6:
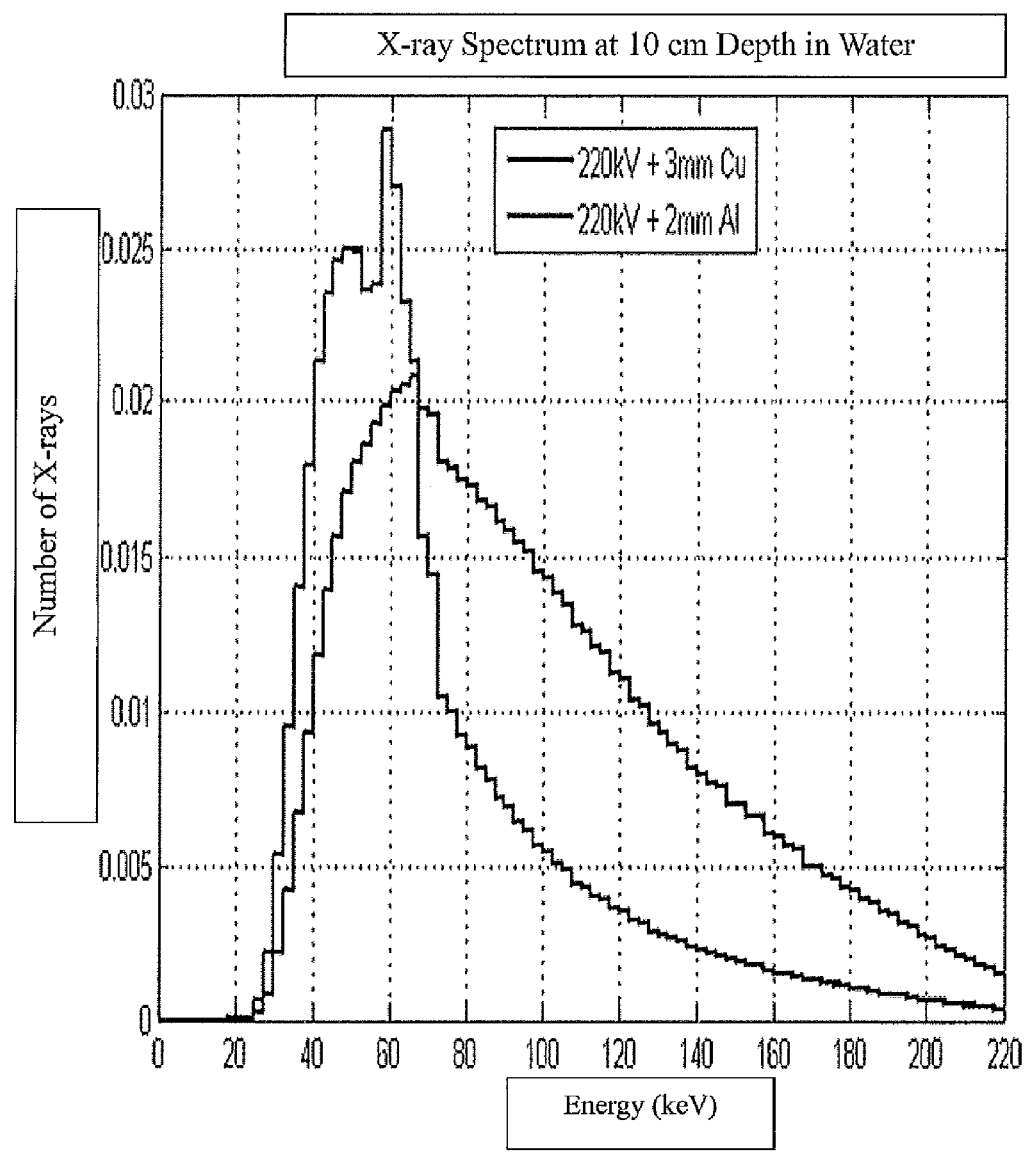
FIG. 6 shows X-ray spectra at different depths in a medium irradiated by said spectrum.

Using the reference and contrast images, the next step is to calculate the radiological distance s for each one of the circular beams to be used, determining the firing position for each one of these according to the two previous criteria; this step corresponds to the second block of the second column in FIG. 8. Note that the number of beams to be used does not necessarily have to be equal to the number of radiation sources given that the apparatus of the present invention allows for the manipulation of these sources in such a way that it is possible to use one source to carry out irradiation of the tumor or malformation from a number of irradiation positions. The number of beams to be used shall be determined by the absorbed dose distribution prescribed by the radio oncologist physician. To determine the appropriate radiation energy for each one of the radiation beams, we must keep in mind that there exists a range of energies which maximize the difference in the X-ray absorption on the part of the contrast agent with respect to the healthy tissue, in such a way that the energy selection process consists of a method which maximizes the number of X-rays reaching the tumor whose energy lies within the range which maximizes the difference in absorption. The following fact is assumed: for each one of the X-ray sources the energy spectrum of the X-rays produced by said source as a function of the maximum energy of the electrons incident on the target as well as the different metallic filters to be used are known. This information can be obtained in an expedited manner by means of, for example, the Monte Carlo simulation of the radiation source. FIGS. 5.1 and 5.2 show, as an example, the X-ray spectrum produced by an X-ray tube and the effect which different filters have on such a spectrum, calculated by means of Monte Carlo simulation. Also by means of Monte Carlo simulation it is possible to learn how the energy spectrum of the X-ray behaves as it travels through a medium, in this case the human body of a patient. FIG. 6 shows as an example both X-ray energy spectra from FIGS. 5.1 and 5.2 at a depth of 10 cm in a water medium, selected here only for illustration purposes and not as a limiting factor given that calculations can be performed for any other medium, obtained by means of Monte Carlo simulation. Based on this information, for a given X-ray source and its initial spectrum, that is, that which is incident on the patient's surface, it is possible to tabulate a series of spectra as a function of the depth in a medium and to determine characteristics such as the average energy as a function of depth or the number of X-rays with energies within a certain range of interest also as a function of depth, just to give a couple of examples. Once tabulated this information can be accessed by, as an example again, a computational algorithm.

With regards to the Monte Carlo simulation applied to the transport of radiation, the interaction radiation with matter is probabilistic in nature, where for each type of interaction its probability of occurrence as a function of the energy, type of radiation and material composition of the medium are known. The Monte Carlo method of radiation transport use random numbers to model in a precise manner how the radiation penetrates through a particular medium, by means of the sampling of the various possibilities of interaction. The medium where the transport of radiation occurs can be any, for example, a patient with tumor malformations. In radiotherapy, the Monte Carlo methods are used to calculate the radiation doses which a patient will receive when being treated with ionizing radiations. While there are other methods to calculate the radiation dose imparted to a patient, the Monte Carlo methods are the most exact and represent the standard to which other methods are compared to.

The procedure to determine the most convenient energy for each one of the radiation beams to be used during treatment, which corresponds to the step in the third block of the second column in FIG. 8, is thus the following:

a. For each source of X-rays a table of values is obtained which indicate the number of X-rays which are found within the energy range of interest as a function of the maximum energy of the electron beam incident on the x-ray tube target and as a function of the available filtration as was previously explained. Note that this table of values needs to be calculated only once and then digitally stored for later use and it is not necessary to undertake the calculations each time a treatment is done.

b. For each combination of maximum energy of the electrons incident on the target and the metallic filtration of each one of the available X-ray sources, a table of values is obtained which indicate the number of X-rays which are found within the desired range of energies as a function of the depth in a medium of interest. Note that this table of values needs to be calculated only once and digitally stored for later use and it is not necessary to undertake the calculations each time a treatment is done.

c. Using the radiologic distances previously determined for each irradiation position of the variable diameter beams, it is then possible to obtain, using the table described in the previous clause b), the combination of maximum energy of the electrons incident on the target and the necessary filtration to obtain the maximum possible number of X-rays with energies in the desired range.

d. The next step is that of computing the radiation dose for each one of the radiation beams to be used during the treatment, this step corresponds to the fourth block of the second column in FIG. 8. This can take place by means of analytic algorithms based on the characteristics of the interaction between the radiation and the matter or by means of Monte Carlo methods of radiation transport.

e. The step which follows is to determine the irradiation times for each one of the beams used in the treatment of the tumor or malformation, this step corresponds to the fifth block of the second column in FIG. 8. Irradiation time is understood as the time necessary during which each one of the beams to be used is emitting X-rays from the assigned irradiation position according to the criteria previously described. This can be achieved through the use of optimization algorithms such as the Cimmino algorithm, to give an example, or any other algorithms available in the literature.

This completes the planning stage of the treatment. The process of treatment planning renders the following data which shall be used by the apparatus object of the present invention to carry out the irradiation of the tumor or malformation:

i. For the rotational X-ray source on a plane surrounding the patient: at each point of the rotation around the patient the planning will arrive at an electronic table such as is shown in the following table:

TABLE 1

| Angle | Time | X-ray spectrum | Collimation | Filtration |
|---|---|---|---|---|
| 0° | $T_1$ | Maximum Energy | Collimation Data | Type of filter |
| ... | ... | ... | ... | ... |
| ... | ... | ... | ... | ... |
| ... | ... | ... | ... | ... |
| 360° | TN | Maximum Energy | Collimation Data | Type of filter | ii. For the circular radiation beams: for each one of the beams to be used the planning will render an electronic table such as is shown in the following. The irradiation positions and directions are established according to an arbitrary reference frame which can be defined, as an example, in relation to the coordinates of the image acquisition system:

TABLE 2

| Irradiation position | Time | Irradiation Direction | X-ray Spectrum | Collimation | Filtration |
|---|---|---|---|---|---|
| $(X_1, Y_1, Z_1)$ | $T_1$ | $(U_1, V_1, W_1)$ | Maximum Energy | Diameter | Type of Filter |
| $(X_2, Y_2, Z_2)$ | ... | $(U_2, V_2, W_2)$ | ... | ... | ... |
| ... | ... | ... | ... | ... | ... |
| $(X_N, Y_N, Z_N)$ | $T_N$ | $(U_N, V_N, W_N)$ | Maximum Energy | Diameter | Type of Filter |

The step which follows is the administration of the treatment to the patient where the apparatus, object of the present invention uses the data rendered by the planning system in order to carry out the treatment.

The Irradiation of the Patient with the Apparatus Object of the Present Invention The apparatus object of the present invention is described as follows. It consists of the following components, as is shown in FIGS. 1A, 1B, 2 and 3, which allow the carrying out of irradiations such as has been described in the process of treatment planning:

Control Computer (8) which coordinates and directs the interactions between the different processes and activities which form part of the treatment, such as is shown in the diagram in FIG. 7, and which consist of the gathering and registering of the three-dimensional radiologic images, the planning of the treatment, the irradiation of the tumor based on the planned treatment, as well as the registering and comparison of the radiologic images obtained during the treatment.

Image Acquisition System (1) which is shown in FIG. 1A, and it could be of the Computerized Axial Tomography (CAT) type, Nuclear magnetic Resonance type or Cone Beam Computed Tomography. Preferably, the three-dimensional acquisition system is a Computerized Axial Tomography (CAT) scanner, and this will be taken as the preferred embodiment in the description which follows.

Support System (6) for the patient with the capability of moving both horizontally as well as vertically and thus allow positioning of the patient according to what was established during the treatment planning phase.

Figure 3:
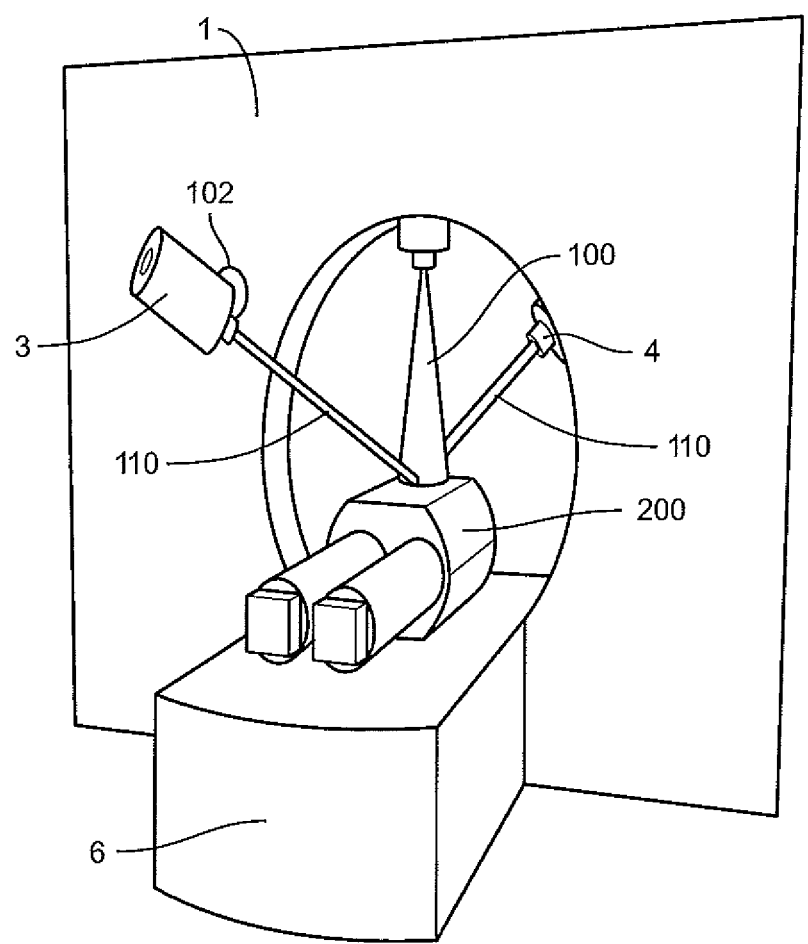
FIG. 3 shows an example of a patient's irradiation using the technique and apparatus of the present invention.

X-ray tube (5) which turns on a plane around the patient, such as is shown in FIGS. 1A and 3. In the preferred embodiment, this X-ray tube is in addition to the X-ray tube used by the CAT scanner to acquire the three dimensional images. It is understandable that this is not necessarily the case, and the specialist in the subject will understand that the same X-ray tube may be used for both purposes provided that a suitable collimation system is attached to such an x-ray tube.

Collimation System (9) for the X-ray tube from the previous point which allows the radiation beams to be defined in adjustment to the geometric shape of the tumor or malformation. This type of collimation system can consist, for example, of a computerized multi-leaf collimator.

A plurality of X-ray sources, two at a minimum, set in a configuration as is shown in FIGS. 1A, 1B and 3, where each one of said sources is identified by the number (3). This plurality of X-ray sources is equipped with a tubular collimator (4) which produces circular radiation beams with a diameter in the, as an example, 0.5 cm to 2 cm range. Note that in FIG. 1B at least one of these X-ray sources (3) is placed in the back part of the discussed apparatus, in such a way that, in conjunction, said sources are capable of irradiating the patient from a plurality of directions.

Figure 2:
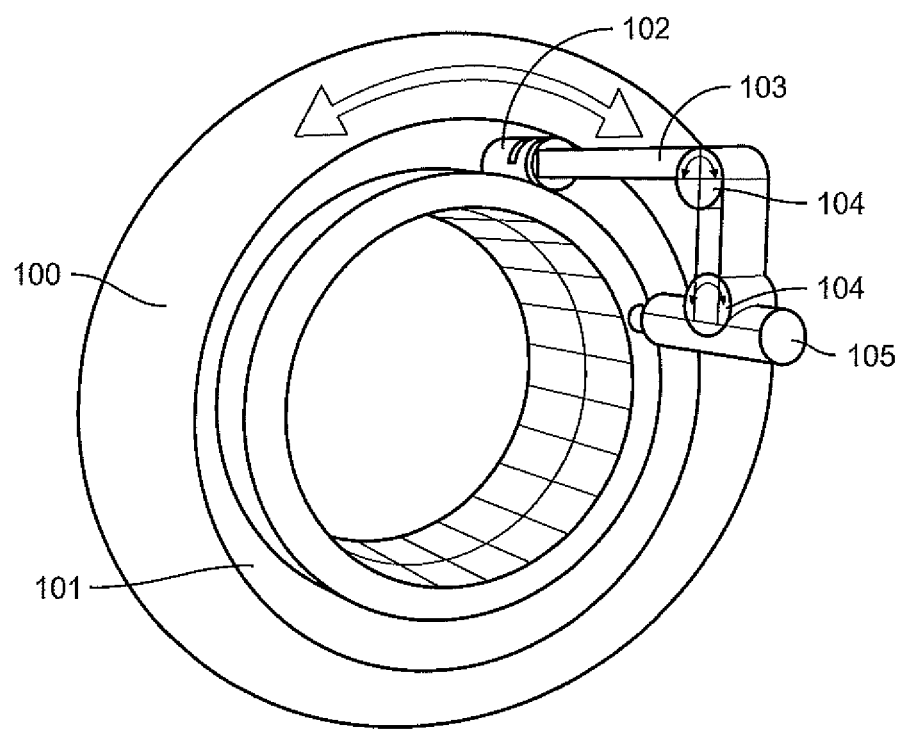
FIG. 2 shows a detailed configuration and the degrees of freedom of one of the X-ray generating systems mounted unto one of the mechanical arms.

A plurality of mechanical arms (103), whose movement has several degrees of freedom as shown in detail in FIG. 2. For each one of the X-ray sources (3), described previously there is a mechanical arm (103). Said plurality of mechanical arms allow for the positioning of the X-ray tubes (103) in a series of positions not necessarily contained on a single plane, according to the resulting requirements determined in the treatment planning previously described. This is achieved according to the numbering shown in FIG. 2, by the rotational mechanisms (102) and (104). Additionally, note that the whole set of mechanical arms (103) and X-ray tube (105) can be moved in a circular manner through the channeled trajectory (101) which forms part of the support base (100). In the same FIG. 3, the circular radiation beams (110) are shown.

The system additionally contains a group of sensors placed in the X-ray tubes which are mounted on the mechanical arms to monitor the patient's position and avoid collisions (not shown). These sensors can be optical or piezo-electric transductors (ultrasound).

The process of irradiating the patient is the following and is explained with the aid of the flow diagram in FIG. 8:

The data rendered by the planning system (7) are transferred to a central computer (8) which serves as the control of the apparatus object of the present invention; this step corresponds to the sixth block of the second column in FIG. 8. The data includes:

The data table corresponding to the rotational X-ray source (5) described in Table 1.

The data corresponding to the plurality of X-ray sources with circular collimation described in Table 2.

The first step is to position the patient (200) using the reference system established at the time of obtaining the radiologic images. To achieve this, the support (6) is operated in such a way that it allows the placement of the patient in the appropriate position. This step corresponds to the first block of the third column in FIG. 8.

The control computer (8) is then charged with positioning each one of the radiation beams to be used in the treatment according to what was established in the two data tables previously described. This step corresponds to the second block of the third column in FIG. 8.

Once the patient (200) has been positioned, and once each one of the X-ray sources has been placed in an initial irradiation position, then the patient is irradiated according to the scheme obtained during the treatment planning phase. This corresponds to the two blocks in the third position of the third column in FIG. 8.

During the application of radiation to the patient, movements can occur, generally involuntary, which may cause the tumor to shift to a position outside of the treatment field. This is a serious problem in radiotherapy, given that then the tumor does not receive the prescribed dose. To avoid this, it is necessary to periodically verify that the tumor be in the proper position, in such a way that the planned treatment can achieve a high degree of success. Additionally, as in this case the absorbed dose at a given point depends on the concentration of the contrast agent at said point, it is necessary to determine the concentration of the contrast agent as the treatment proceeds, in such a way that the treatment plan can be modified if the contrast agent concentration should change significantly at a given point in time during the treatment. To address this problem, the present invention, through the acquisition of three-dimensional radiologic images is capable of monitoring in real time both the position of the tumor and the concentration of contrast agent present in the irradiated volume. This corresponds to the fourth block of the third column of the diagram shown in FIG. 8. Two alternatives are possible:

The verification of the tumor position takes place in an automatic fashion during the irradiation of the patient after certain time period lapses from the last verification. This time period can be selected by the equipment's operator before starting the treatment. By automatic verification, it shall be understood that the apparatus object of the present invention, without any intervention by the operator, takes the necessary steps to obtain a three-dimensional radiologic image, transfers it to the central control computer where it is compared to the previous image to both determine the position of the tumor with respect to the reference frame as well as to determine the distribution of the contrast agent.

In an alternative manner, the operator of the equipment can decide, if he/she should consider it medically necessary, direct the apparatus object of the present invention, by means of sending a command to the central control computer, to perform a verification of the tumor position and the distribution of the contrast agent by means of obtaining a three-dimensional radiologic image. In both cases, the steps which follow once it is decided a new three-dimensional image of the patient is needed, are initiated by the circular connector 1 in the fourth block of the third column of the diagram in FIG. 8.

Following the flow diagram in FIG. 8, the newly obtained verification image is transferred to the planning computer (7) where it is compared to previous images to decide if the tumor is in the appropriate position, this being the position for which the treatment was planned for, or if the concentration of contrast agent has changed in a significant way. This again corresponds to blocks 3 through 8 of the first column of the diagram in FIG. 8.

If it is determined that the position of the tumor position is adequate, then the patient treatment continues as planned. This corresponds to the circular connector 4 of the diagram in FIG. 8.

If it is determined that the position of the tumor is not adequate according to the treatment plan or that the concentration of the contrast agent has significantly changed, a recalculation of the absorbed dose needs is undertaken for each one of the radiation beams which have not yet been applied unto the patient. This corresponds to the circular connector 5 of the diagram in FIG. 8.

The treatment is continued until verification of the position of the tumor or of the concentration of the contrast agent within the tumor is needed. This corresponds to the circular connector 3 of the flow diagram in FIG. 8.

Once each of the radiation beams determined by the treatment plan has imparted the necessary radiation dose to accomplish the treatment objectives according to the physician, the treatment is ended. This corresponds to the fifth block of the third column in the diagram in FIG. 8.

What is claimed is:

1. Method to carry out image-guided radiotherapy with kilovoltage X-ray beams in the presence of contrast agents, characterized because it consists of the following stages: a) Determining the patient's geometry and the concentration of the contrast agent in each point of the same, b) treatment planning and c) irradiation of the tumor or malformation, wherein a) comprises: the obtaining of a three dimensional image of a portion of the patient to be treated by means of a 3D image acquisition system, which is used as a reference image; the administering of the contrast agent to the patient; the taking of a second 3D image with the same acquisition parameters as the previously described reference image, the subtracting of the reference image from the image obtained with the contrast agent to obtain a residual image due the presence of the contrast agent in the patient, the so-called concentration image; by means of a calibration curve, to each pixel of the residual image a concentration of contrast agent is assigned according to the value of the signal present in said pixel; using the reference image in conjunction with the concentration image to carry out the treatment planning; b) comprises; selecting the number of radiation beams, angles of incidence on the tumor and the energy of the beam in order to accomplish a minimum dose imparted onto the tumor and a maximum allowable dose imparted to the structures and healthy tissue surrounding the tumor, using two types of available radiation beams in a simultaneous manner during the treatment of the tumor or malformation, a radiation beam produced by a kilovoltage X-ray source with a capability to rotate on a plane around the patient and a plurality of circular X-ray radiation beams produced by kilovoltage X-ray sources with a variable diameter, using two types of radiation beams simultaneously or separately, whichever is more convenient for the purposes of the treatment goals; determining the parameters to be used in each one of the beams to be used in the treatment: i) collimation, ii) determining of the irradiation positions for each source, iii) determining the convenient energy for each radiation beam, iv) computing the radiation absorbed dose, and v) determining the irradiation times for each beam; c) comprises: positioning the patient using the reference system established at the time of obtaining the radiologic images; positioning each one of the radiation beams to be used during the treatment; irradiation with rotational beam; irradiation with circular beams; verifying at different time intervals that the tumor remains in the correct position; determining the concentration of the contrast agent along the length of time of the treatment; monitoring in real time the position of the tumor; transferring the verification images obtained to the computer charged with planning and registering of images, comparing these to the previous images to decide if the tumor is found at an appropriate position; continuing with the irradiation if the tumor position is correct; recalculating the absorbed dose for each one of the radiation beams not yet applied to the patient if it is determined that the tumor is not in the position for which the treatment was developed for or if the concentration of the contrast agent has changed significantly; continue with the treatment until another verification of the tumor position or concentration of the contrast agent in the tumor is necessary; finish the treatment once each one of the radiation beams determined by the treatment plan have imparted the radiation dose necessary to accomplish the treatment objectives set by the physician.

2. Method to carry out image-guided radiotherapy with kilovoltage X-ray beams in the presence of contrast agents, according to claim 1, characterized because the calibration curve is obtained previously using known concentrations of a contrast agent embedded in anthropomorphic phantoms, which are scanned with a Computerized Tomography scanner to obtain images of each element into which the contrast agent solutions are deposited; plotting each pixel signal against the known concentration of the contrast agent to obtain a calibration curve.

3. Method to carry out image-guided radiotherapy with kilovoltage X-ray beams in the presence of contrast agents, according to claim 1, characterized because the determination of the irradiation positions for a plurality of circular beams with varying diameter takes place in a computerized manner using the following two criteria:
   a. To reduce the radiation dose to the skin the beams are not allowed to cross or intersect on the surface of the subject to be irradiated.
   b. The chosen position of irradiation for each beam must be such that the radiologic distance from the surface of the patient to the site of the tumor or malformation is minimized.

4. Method to carry out image-guided radiotherapy with kilovoltage X-ray beams in the presence of contrast agents, according to claim 1, characterized because the determination of the most convenient energy for each one of the radiation beams to be used in the treatment follows the following stages: a. For each x-ray source a table of values is obtained which indicate the number of x-rays which are found within the energy range of interest as a function of both the maximum energy of the electron beam incident on the target and the available filtration; b. Obtain for each combination of maximum energy of electrons incident on the target and metallic filtration of each one of the available X-ray sources, a table of values which indicate the number of X-rays which are found within the desired energy range as a function of the depth of a medium of interest; c. Once the radiologic distance of each one of the variable diameter beams which travels from the surface to the site of the tumor or malformation has been determined, then using the table described in the previous clause b, the maximum energy combination of the electrons incident on the target and the necessary filter are selected to obtain the maximum number possible of X-rays with energies in the rage of interest at a given depth.

5. Method to carry out image-guided radiotherapy with kilovoltage X-ray beams in the presence of contrast agents, according to claim 1, characterized because the step of computing the radiation dose produced for each one of the radiation beams to be used during the treatment, takes place by means of analytic algorithms based on the interaction characteristics between the radiation and the matter or by means of Monte Carlo methods of radiation transport.

6. Method to carry out image-guided radiotherapy with kilovoltage X-ray beams in the presence of contrast agents, according to claim 1, characterized because the treatment planning process produces the following data which are used by the apparatus of claim 1 to carry out irradiation of the tumor or malformation: i. For the rotational X-ray source on a plane around the patient: at each point of the rotation surrounding the patient the planning produces an electronic table with values of angle, time, X-ray spectrum, maximum energy, collimation data, types of filter; ii. for the circular radiation beams: for each one of the beams used the planning produces an electronic table with the following values: irradiation position, irradiation direction, which are established in reference to an arbitrary reference frame, X-ray spectrum, collimation data and filtration data.

7. Method to carry out image-guided radiotherapy with kilovoltage X-ray beams in the presence of contrast agents, according to claim 1, characterized because the patient's irradiation process comprises transferring the data produced by the planning system to the central computer which acts as the control of the apparatus of claim 1, the data includes those which are produced according to claim 6.

8. Method to carry out image-guided radiotherapy with kilovoltage X-ray beams in the presence of contrast agents, according to claim 1, characterized because the patient's irradiation process comprises: the operation of the patient support to place the patient in the appropriate place, and afterwards through the use of the control computer, position each one of the radiation beams which will participate in the treatment according to what was established in the two data tables according to claim 6.

9. Method to carry out image-guided radiotherapy with kilovoltage X-ray beams in the presence of contrast agents, according to claim 1, characterized because the process of the patient's irradiation comprises the use of three-dimensional radiologic images to verify both the position of the tumor and the concentration of the contrast agent in real time during the irradiation of the patient either automatically after a certain time interval lapses from the last verification or in an alternative manner, at the request of the operator of the apparatus.

10. Apparatus to carry out image-guided radiotherapy with kilovoltage X-ray beams in the presence of contrast agents, according to claim 1, characterized because it consists of: a system for obtaining three-dimensional images of a patient; a plurality of X-ray generating sources which consist of an X-ray tube which turns on a plane around the patient, a plurality of X-ray sources, at least two, set one on a plane anterior to the X-ray tube that rotates in a plane and others on a posterior plane to said X-ray tube, where at least one of these sources is placed on the back part of the apparatus, in such a way that, in conjunction, said sources are capable of irradiating the patient from a plurality of directions; a plurality of tubular circular collimator, with which the plurality of X-ray sources are equipped to define the radiation beams in order to made them incident on the tumor or malformation; a plurality of mechanical arms, one mechanical arm for each one of the X-ray sources that produce the circular beams, which place the X-ray tubes in a series of positions on one or more planes, by means of rotational mechanisms the whole mechanical arm assembly and X-ray tube are moved in a circular manner through a channeled trajectory which forms part of its support base; a group of sensors placed in the X-ray tubes which are mounted on the mechanical arms to monitor the patient's position and avoid collisions; a computer control system which coordinates and directs the interaction between all the different processes and activities which form part of the treatment, which consist of obtaining and registering the three-dimensional radiologic images, the planning of the treatment, the irradiation of the tumor based on the treatment plan, as well as the registration and comparison of the radiologic images obtained during treatment and a support system for the patient capable of moving both horizontally as well as vertically and thus allow the positioning of the patient according to that which was established during the treatment planning.

11. Apparatus to carry out image-guided radiotherapy with kilovoltage X-ray beams in the presence of contrast agents, according to claim 10, characterized because the system for the acquisition of three-dimensional images obtains, among others, a three-dimensional image of a portion of the patient to be treated, this image provides information on the geometry of the place to be irradiated, and is also used by the computer to establish the position of each one of the structures of interest as related to a frame of reference and serves also as a reference to determine the amount of contrast agent present in each one of the organs and tissues of interest once the contrast agent is administered to the patient.

12. Apparatus to carry out image-guided radiotherapy with kilo-voltage X-ray beams in the presence of contrast agents, according to claim 10, characterized because the system for obtaining three-dimensional images is of a Computerized Axial Tomography type, Nuclear magnetic resonance or Cone Beam Computed Tomography; in the preferred embodiment the system for obtaining three-dimensional images is a Computerized Axial Tomography scanner.

13. Apparatus to carry out image-guided radiotherapy with kilovoltage X-ray beams in the presence of contrast agents, according to claim 10, characterized because the X-ray generating sources produce a radiation beam which has the capability of producing different energy spectra and a plurality of circular radiation beams with a variable diameter, this plurality of radiation beams has the capability of producing different energy spectra; these two types of radiation beams can be used simultaneously or separately, according to what is more convenient for the treatment purposes.

14. Apparatus to carry out image-guided radiotherapy with kilovoltage X-ray beams in the presence of contrast agents, according to claim 10, characterized because the tubular collimator produces circular radiation beams with diameters in the 0.5 cm to 2 cm. range, this plurality of radiation beams produces different energy spectra by means of varying the maximum energy of the electrons which knock against the metallic target or by means of using different metallic filters of differing materials and thicknesses placed in the exit window of the X-ray generator.

15. Apparatus to carry out image-guided radiotherapy with kilovoltage X-ray beams in the presence of contrast agents, according to claim 10, characterized because the collimator of the X-ray source produces radiation fields which are adjustable to the geometric shape of the tumor, as seen from the beam's eye view, the radiation beam produces continuously varying energy spectra by means of varying the maximum energy of the electrons which knock against the metallic target or by the use of metallic filters made of different materials and thickness placed on the exit window of the X-ray generator.

* * * * *